United States Patent [19]

Pruitt

[11] Patent Number: 4,941,623
[45] Date of Patent: Jul. 17, 1990

[54] STAPLING PROCESS AND DEVICE FOR USE ON THE MESENTERY OF THE ABDOMEN

[75] Inventor: J. Crayton Pruitt, St. Petersburg, Fla.

[73] Assignee: United States Surgical Corporation, Norwalk, Conn.

[21] Appl. No.: 456,361

[22] Filed: Dec. 26, 1989

Related U.S. Application Data

[63] Continuation-in-part of Ser. No. 350,758, May 12, 1987, which is a continuation-in-part of Ser. No. 237,433, Aug. 26, 1988, Pat. No. 4,848,637, which is a continuation-in-part of Ser. No. 60,469, Jun. 11, 1987, abandoned, which is a continuation-in-part of Ser. No. 864,336, May 19, 1986, abandoned.

[51] Int. Cl.$^5$ ................................................ B31B 1/00
[52] U.S. Cl. ........................................ 227/19; 227/175; 606/219
[58] Field of Search ........... 606/219; 227/19, 175–182

[56] References Cited

U.S. PATENT DOCUMENTS

| | | | |
|---|---|---|---|
| 3,252,643 | 5/1966 | Strekopytov et al. | 227/19 |
| 3,795,034 | 3/1974 | Strekopytov et al. | 227/19 |
| 3,958,738 | 5/1976 | Tremblay | 227/109 |
| 4,606,345 | 8/1986 | Dorband et al. | 227/181 |
| 4,667,865 | 5/1987 | Judge | 227/109 |
| 4,715,520 | 12/1987 | Roehr, Jr. et al. | 227/19 |
| 4,848,637 | 7/1989 | Pruitt | 227/19 |

Primary Examiner—Randall L. Green
Assistant Examiner—Gary Jackson
Attorney, Agent, or Firm—Walter J. Monacelli

[57] ABSTRACT

The process, stapler and stapler cartridge described herein comprise those suitable for stapling a patient's mesentery and omentum with two, three or four rows of staples, the rows being substantially parallel to each other, the staples in all the rows having the same crown size with alternate rows staggered one-fourth of the length of each crown with respect to the adjacent crown in the adjacent row or rows of staples. Advantageously the prong lengths in at least one row differ from the pront lengths in the other row or rows. Advantageously the longer prongs are 30-100 percent larger, preferably about 33-75 percent larger than the smaller prongs. This arrangement is capable of satisfactorily sealing off the variety of sizes of blood vessels and holding firmly the fatty tissue found in the mesentery and in the omentum. Other arrangements of staples have been designed to effect similar results in the mesentery in which the staples having smaller and larger prongs are arranged alternately in the same row so that the gaps between staples are covered by staples staggered one-fourth of the crown length with respect to staples in an adjacent row of staples.

18 Claims, 12 Drawing Sheets

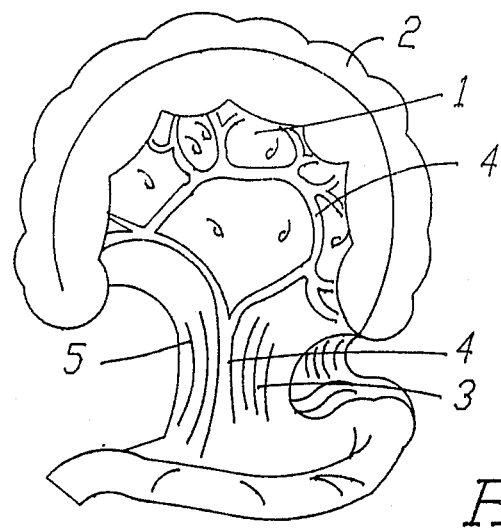
Fig_1
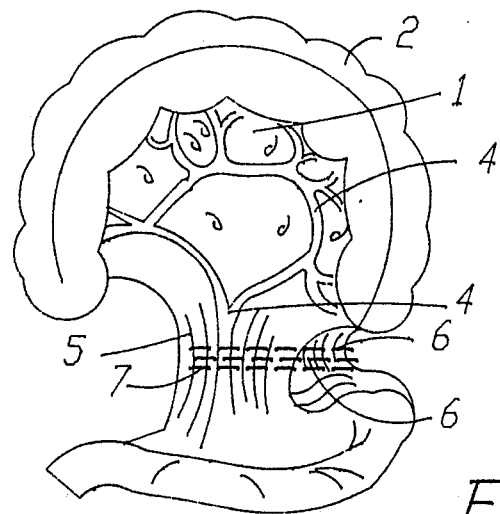
Fig_2

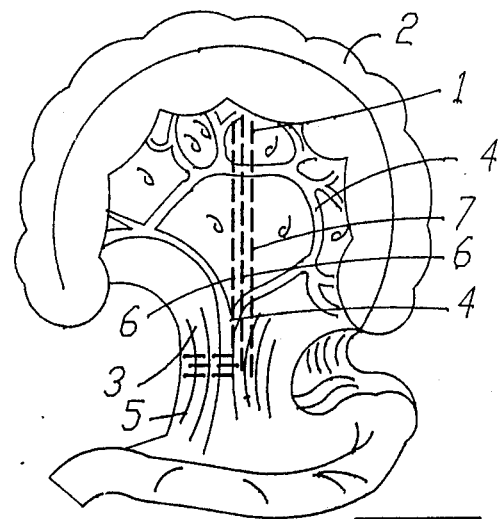
*Fig_3*
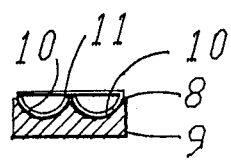 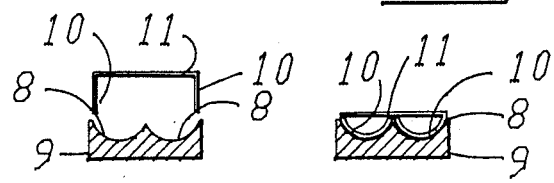
*Fig_4*   *Fig_5*
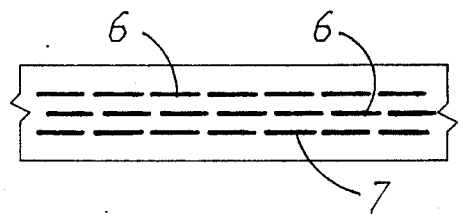
*Fig_6*

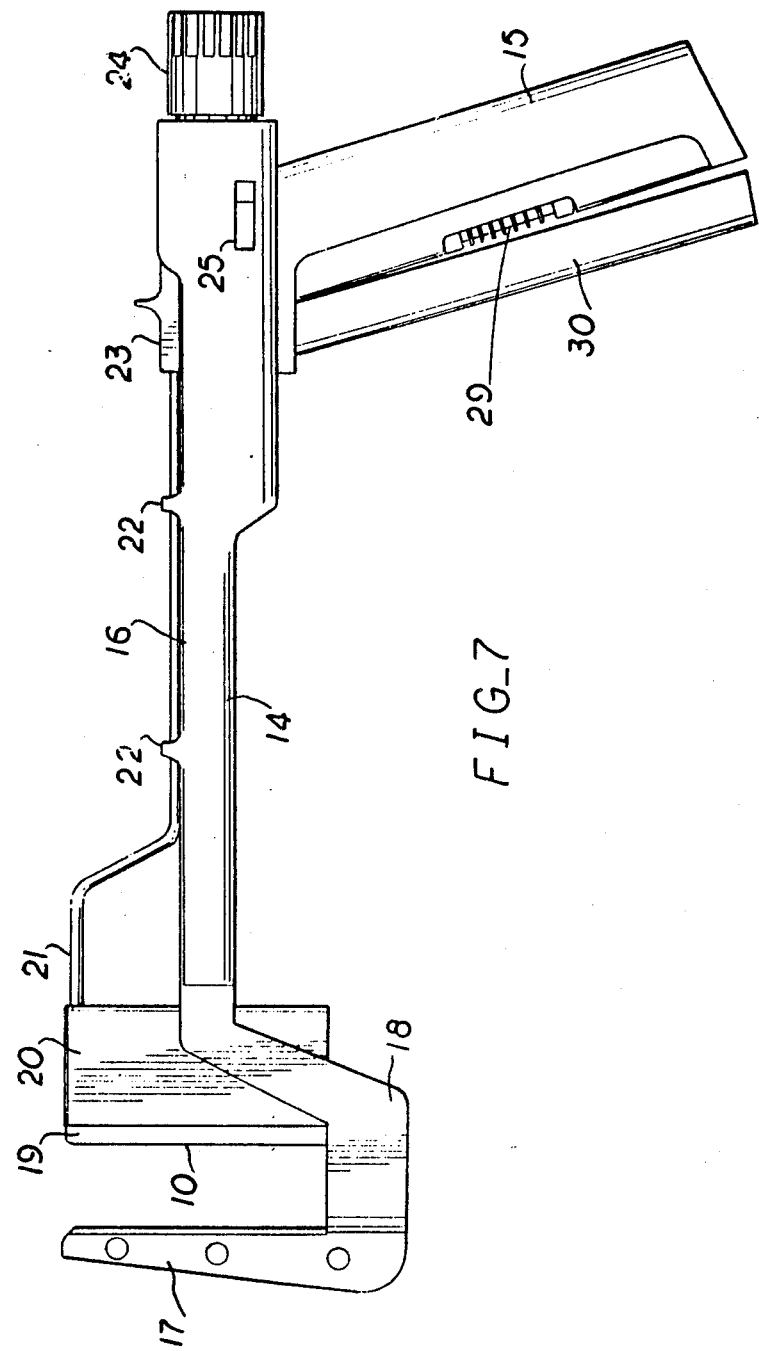
FIG_7

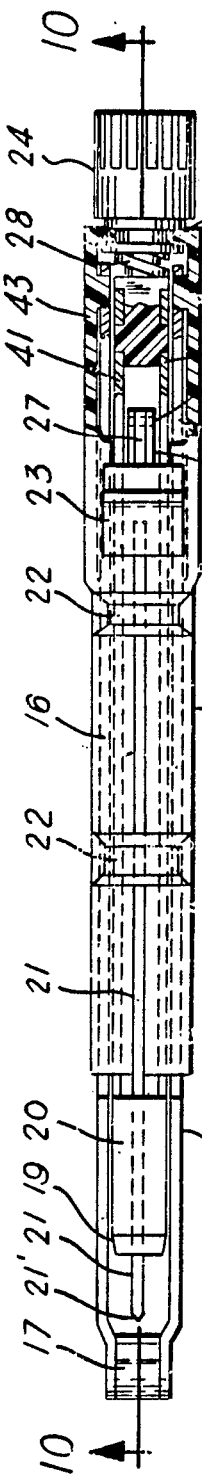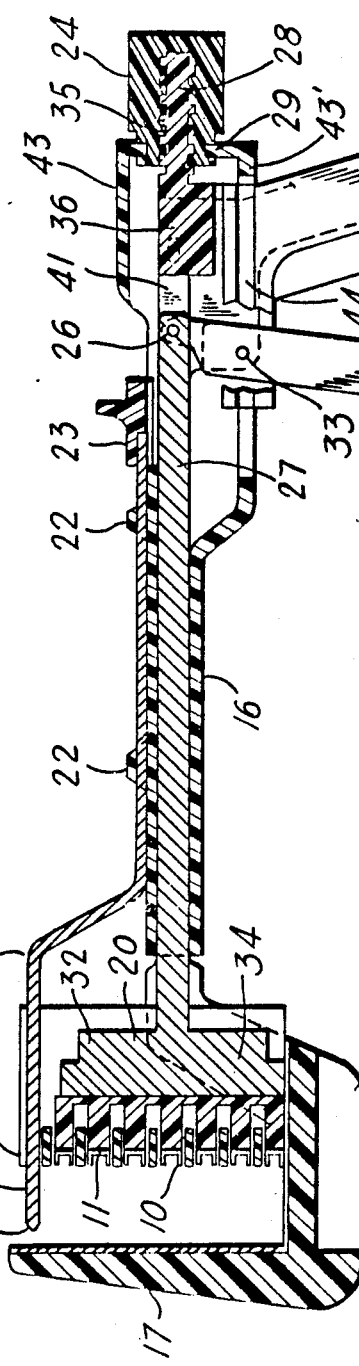
FIG.9
FIG.10

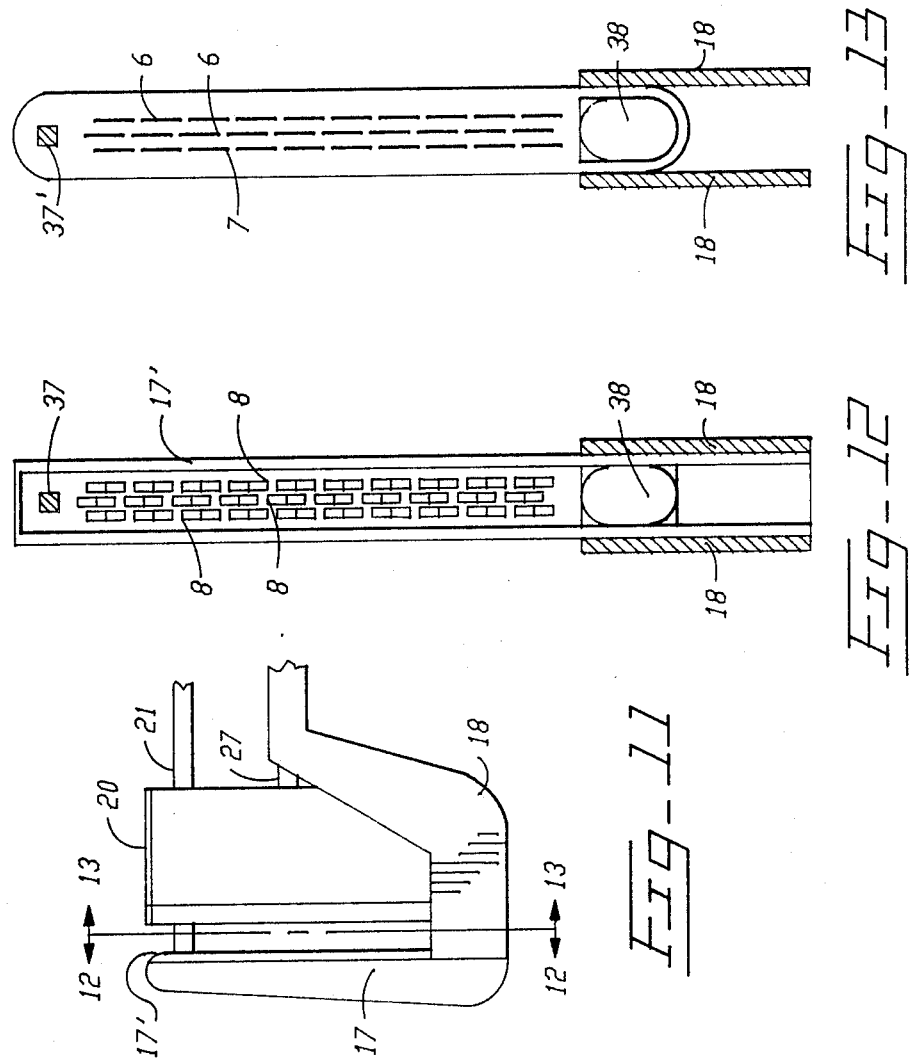

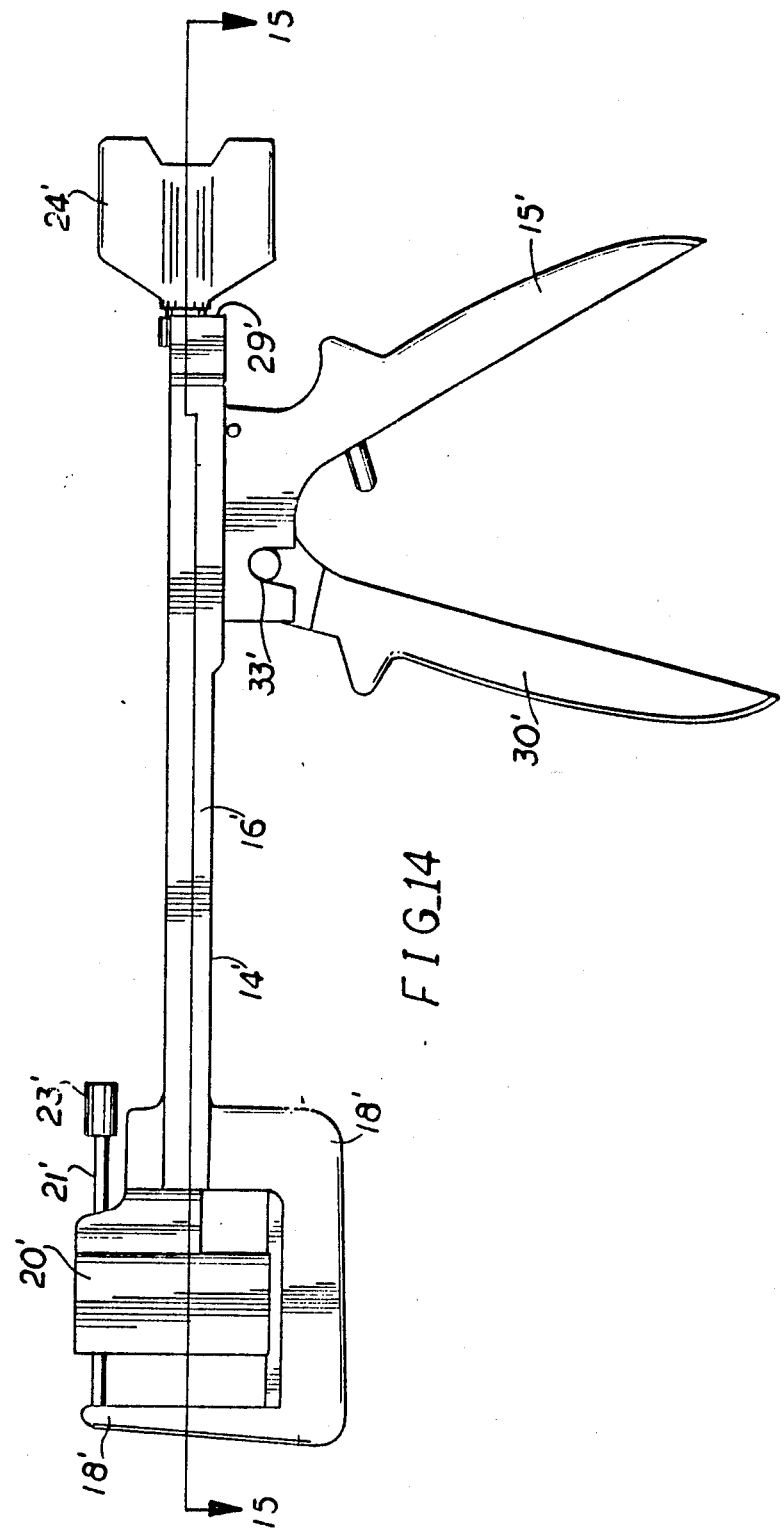

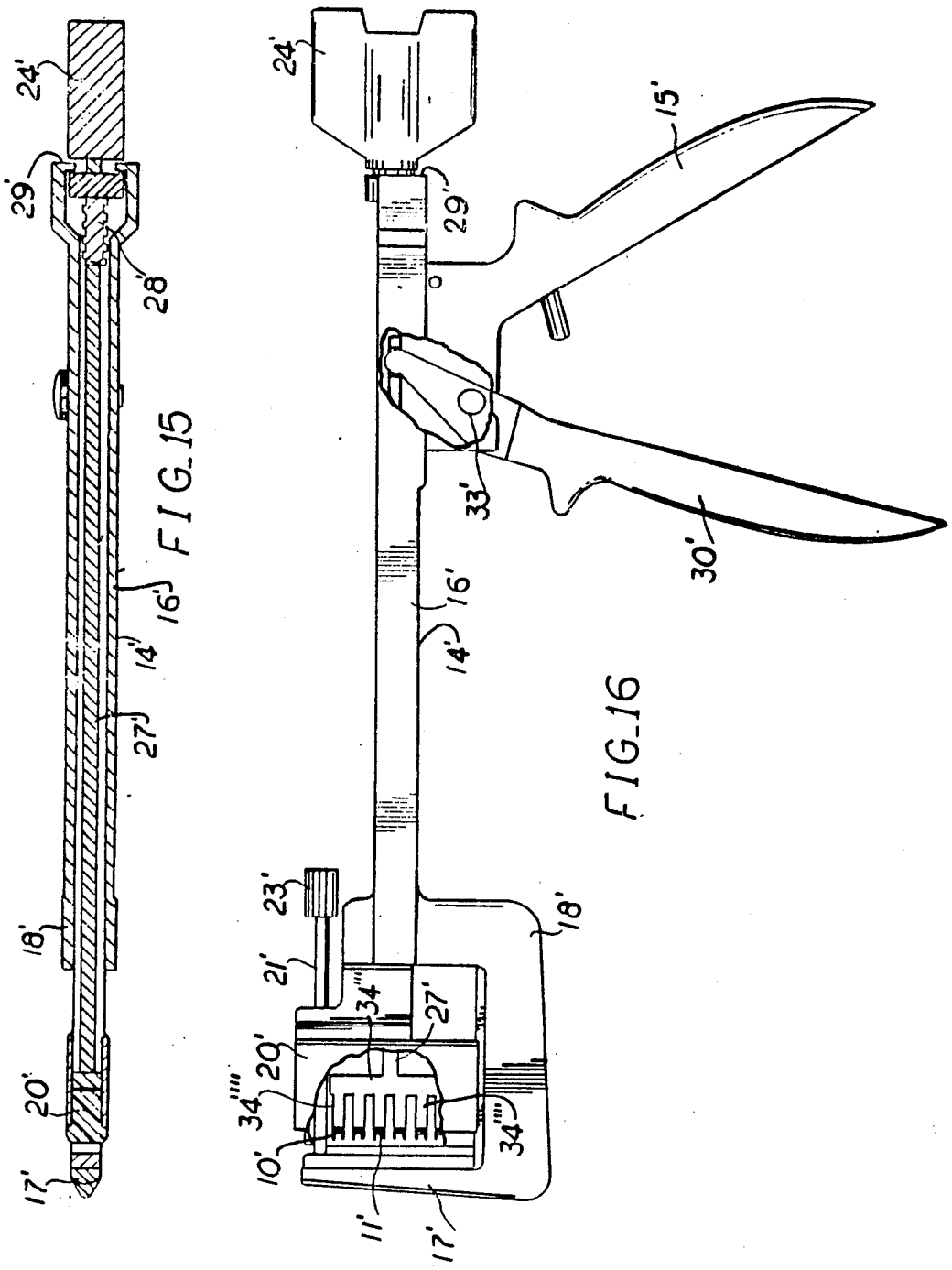

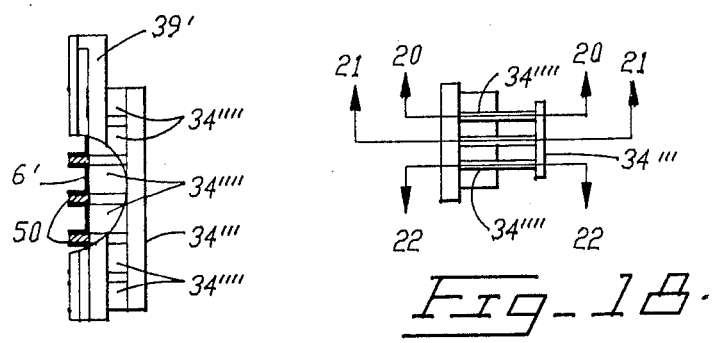
Fig_17  Fig_18
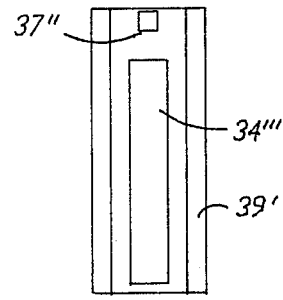
Fig_19
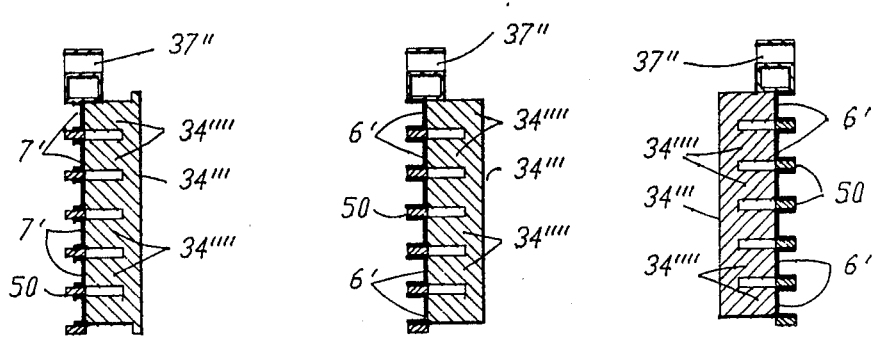
Fig_20  Fig_21  Fig_22

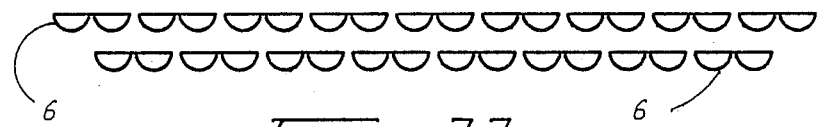
Fig_23
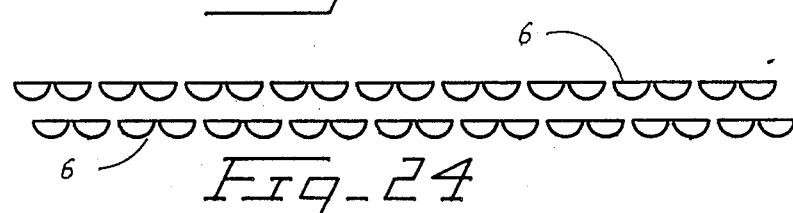
Fig_24
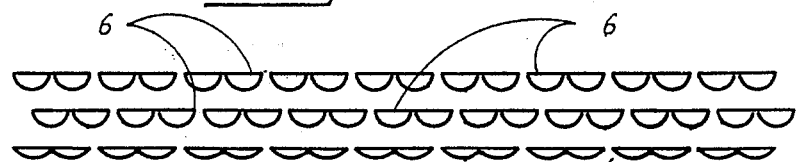
Fig_25
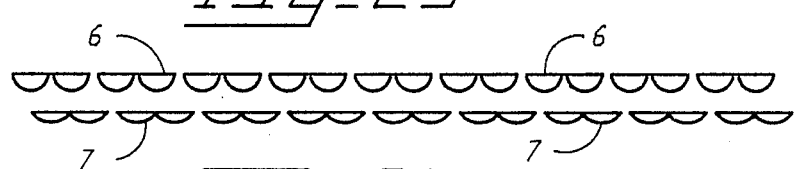
Fig_26
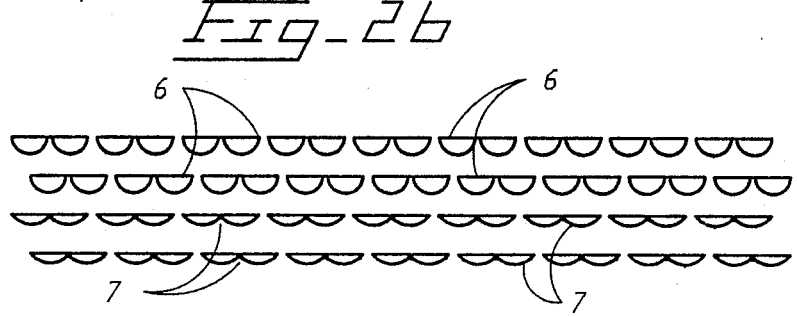
Fig_27

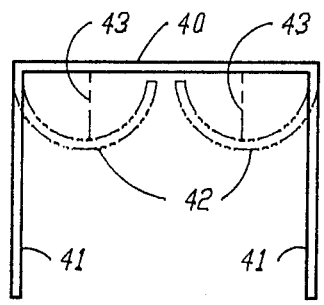
Fig_28
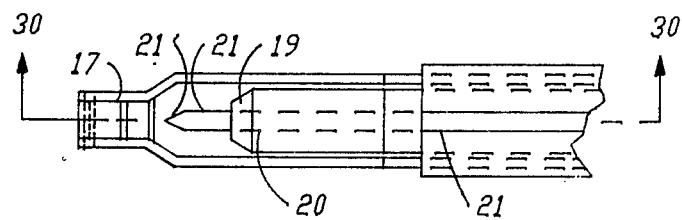
Fig_29
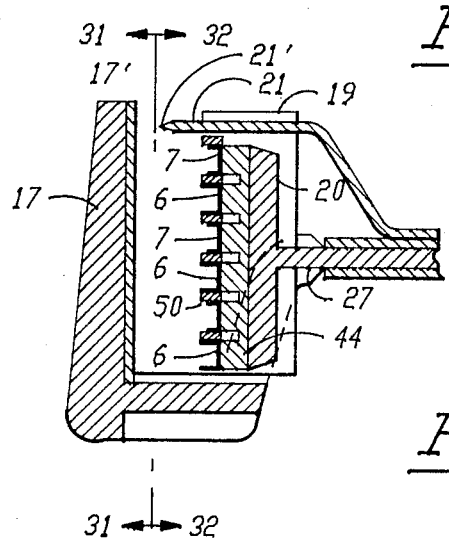
Fig_30

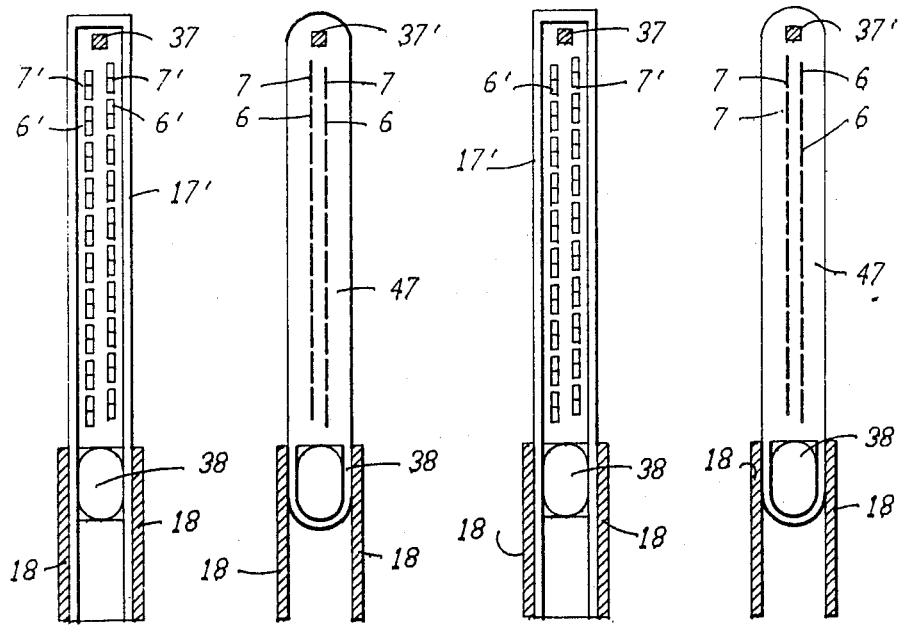
Fig_31  Fig_32  Fig_33  Fig_34
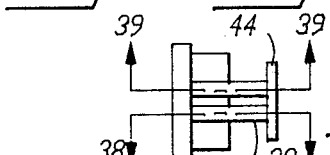
Fig_36
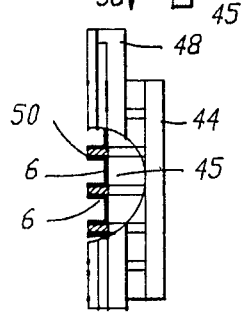 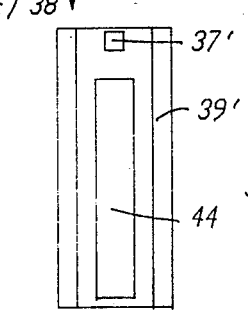 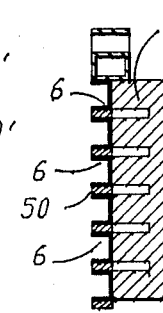 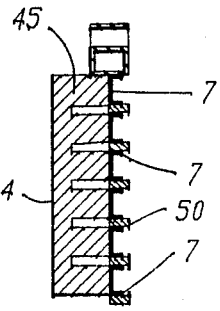
Fig_35  Fig_37  Fig_38  Fig_39

STAPLING PROCESS AND DEVICE FOR USE ON THE MESENTERY OF THE ABDOMEN

This application is a continuation-in-part of copending application Ser. No. 07/350,758 filed May 12, 1989, which is a continuation-in-part of application Ser. No. 07/237,433, filed Aug. 26, 1988, issued on July 18, 1989 as U.S. Pat. No. 4,848,637, which in turn is a continuation-in-part of application Ser. No. 07/060,469, filed June 11, 1987, now abandoned, which in turn is a continuation-in-part of Ser. No. 06/864,336 filed May 19, 1986, now abandoned.

FIELD OF THE INVENTION

This invention relates to a device for stapling the mesenteries of a patient's abdomen. More specifically this invention relates to a process for use in the mesenteries of a patient's abdomen of applying rows of staples of the same crown size with the staples in alternate rows staggered by one-quarter of the crown size with staples in the adjacent row or rows. Still more specifically it relates to a stapler for applying two, three or four rows of staples of the same crown size with at least one row varying in prong size from the size of prongs in the other row or rows and designed to be applied to the fatty tissue of the mesenteries so as to seal off the blood vessels of varying size therein. It relates also to similar results from two, three or four rows of staples of the same crown size in which staples of large and small prong size are positioned alternately in at least one of said rows of staples.

BACKGROUND OF THE INVENTION

The stomach, appendix, jejunum, ileum, ascending colon, transverse colon, descending colon, liver and spleen are attached to the posterior part of the abdominal wall by mesenteries which carry blood vessels and lymphatics to and from these organs. The mesenteries also contain lymph nodes. The mesenteries vary in thickness, but all contain large amounts of fatty tissue and blood vessels which vary in size from 1.0 cm. in diameter down to less than 0.1 mm. in diameter. The greater omentum is a double fold of mesentery and it too carries large numbers of blood vessels of varying size, and the thickness of the greater omentum is quite variable from one patient to another.

There are stapling devices for closing the bronchus, pulmonary artery, pulmonary veins, for closure of the large or small intestine, for closure of the stomach or stapling of the stomach for morbid obesity, for end-to-end anastomosis of the intestines, for side-to-side anastomosis of the intestines and for individual ligation and for division of a blood vessel. In addition, there is a variety of occluding clips for blood vessels and skin staplers. Because of the fatty tissue and the variety of sizes of blood vessels present in the mesentery and the omentum, the available staplers are not satisfactory for stapling the mesentery and the omentum. The best stapler only ligates one vessel at a time and it commonly tears blood vessels in the vicinity of its use, requiring time-consuming repairs after ligation of the intended vessel.

U.S. Pat. Nos. 4,606,345 (Dorband et al), 3,252,643 (Strekopytov et al), 3,795,034 (Strekopytov et al), Roehr et al 4,715,520, Tremblay 3,958,738 and Judge 4,667,865 were cited against the parent applications.

The Dorband et al patent describes a stapler gun and a method for stapling two staggered rows of two-part fasteners for joining body tissue with two-part plastic fasteners which are believed to be more suitable for remaining in the patient as compared to stainless steel staples. The device is designed to provide two rows of fasteners, which fasteners may be made of biologically absorbable or non-absorbable polymeric materials. One part of the fastener comprises a U-shaped staple which has legs that are caused to penetrate the tissue. The other part of the fastener is placed on the other side of the tissue and used to engage the legs of the staple and interlock therewith. There is no disclosure of staggering any place other than the midpoint of the staples, nor is there any disclosure of variations in the size of the fasteners, nor is there any discussion of this arrangement being satisfactory for use with a patient's mesentery.

The Strekopytov (U.S. Pat. Nos. 3,252,643 and 3,795,034) teach an older type of device used for applying rows of staples. Neither of these patents make reference to any differences in sizes of the staples in any of the rows nor to any staggering other than at the midpoints of the staples.

The Roehr et al patent shows a stapler which applies three rows of staggered staples. This patent does not show staggering of staples at any other point than the midpoint and the staples in each row are identical in size to the staples in the other rows. There is no reference to any variation in the size of the staples.

Applicant's U.S. Pat. No. 4,848,637 issued on July 18, 1989, and the patent about to issue on allowed application Ser. No. 07/350,758, filed May 12, 1989 describe process, stapler and cartridge suitable for stapling the mesentery and the omentum using two, three or four rows of staples having different crown size in at least one row of staples as compared to the other row of staples, including an arrangement of staples in which the crown size of alternate staples in the same row differ from crown size of the staples in between said alternate staples. This effective arrangement is based on the fact that the staples having larger crowns also have longer prongs and the prongs having smaller crowns have shorter prongs. This is based on the fact that the prong size is determined by the requirement to reach halfway across the bottom of the crown and also to have enough additional length to form a loop under the crown. This loop serves a similar function as a stitch in a suture or ligation used to seal off the blood vessels after an incision has been made in human tissue. The larger the loop is to be the greater will the length of the prong be in excess of that required to reach one-half the length of the crown. With mesentery and omentum a combination of large loops and smaller loops is desired to seal off the flow of blood from the blood vessels severed by the incision. Advantageously each blood vessel and also some fatty tissue to squeeze the blood vessel shut is embraced by a loop of the staple.

When the crown sizes are the same in a number of rows of staples, as provided in commercially available cartridges of staples, the staples in one row are staggered with respect to the staples in the adjacent row or rows. The staggering in each case is effected by positioning the beginning end of the first staple in the second row of staples opposite the midpoint of the first staple of the first row of staples. This means that the midpoint of each of the staples in the second row of staples is opposite a gap between staples in the first row. It also means that the gaps between the staples in the second row are opposite the midpoint of adjacent staples in the first row. The midpoint of the staples is where the ends of the prongs on the underside of those staples come near to each other and in many cases leave a gap between each other and between the prong ends and the crown. In some cases particularly when long prongs are used, the grooves in the anvil have to be deeper with a sharper curvature at the bottom of the groove thereby often causing a curve at the end of the prong which causes a space between the prong ends in their final positions. These conditions mean that blood vessels which come in the gaps between staples in one row will not be encased in a loop in the adjacent row of staples. It also is possible that a blood vessel may be punctured by one or both of the prong ends for a staple or may be in a gap between prong ends and the crown, or even in the space between the upper curvature of the prong loops.

OBJECTIVE OF THIS INVENTION

It is an objective of this invention to provide a process for effectively stapling the mesentery and the omentum.

It is an objective of this invention to provide a stapler and a cartridge therefor which is suitable for stapling the mesentery and the omentum.

It is also an objective of this invention to provide a stapling device with appropriate arrangement of staples which will satisfactorily seal off blood vessels of varying sizes as found in the mesentery and in the omentum.

It is also an objective of this invention to provide an arrangement of staples which provide prong loops opposite gaps or open spaces in an adjacent row or rows of staples.

It is also an objective of this invention to provide an arrangement of staples which provide prong loops opposite prong ends in an adjacent row or rows of staples.

SUMMARY OF THE INVENTION

In accordance with the present invention a new process, a new stapler and a new staple cartridge have been designed suitable for use on the mesentery and on the omentum, the use of which process, stapler and cartridge are capable of effectively stopping the bleeding of blood vessels in that part of the mesentery or of the omentum which is being resected. These are designed to apply two, three or four rows of staples of the same size "crown" or main body portion of the staples, the rows being substantially parallel to each other and the staples in each row being staggered one-quarter of the crown length with the staples in the adjacent row or rows of staples. Advantageously there is at least one row in which the prong lengths of the staples differ from the length of the staple prongs in the other row or rows.

An effective means for cutting off the flow of blood from a blood vessel in the mesentery or omentum is to embrace the blood vessel with a curved loop of an applied staple. This presses the fatty tissue against the wall of the blood vessel, thereby collapsing and sealing off the blood vessel. If the blood vessel is positioned where the two ends of the prongs meet near the middle of the staple, it is possible for the prong end or prong ends to puncture the blood vessel without effecting the desired seal. With many of these staples the prong ends do not reach to the crown and sometimes to each other, so that the resulting gaps result in ineffectiveness in the sealing of blood vessels.

When staples having the same length in the main body portion or "crown" are generally applied in two or three parallel rows, the staples in each row are arranged in a staggered position with respect to staples in the adjacent row or rows. The presently available staplers and cartridges are designed so that the middle of each staple is opposite the gap between staples in the adjacent row or rows. This circumstance may not be in other parts of the body. However in the mesentery and omentery where it has been unsatisfactory to cut off the flow of blood by staples until applicant effected this by the use of staples of different crown sizes and corresponding different prong lengths, as disclosed in applicant's U.S. Pat. Nos. 4,848,637 issued July 18, 1989 and in 4,930,503, issued June 5, 1990. The use of different crown lengths disturbed this regularity of having gaps in one row opposite prong ends in an adjacent row. However if the same crown size is used in all rows but having at least one row of staples with different sized prongs, the same problem of having gaps in each row opposite prong ends in adjacent row or rows again occurs.

With staples of identical crown size, it is found that effective sealing of blood vessels in the mesentery and omentum can be effected by positioning the staples so that the gaps between staples in one row are opposite loops in staples of the adjacent row or rows. This positioning is effected by having the first staple in a second row of staples shifted one-quarter of the length of the staple with respect to the first staple in the first row of staples. This means that in each row each gap between staples is positioned opposite a prong loop in the adjacent row. This also means that there is a loop opposite the prong ends in the adjacent row or rows of staples. If there is a space between these prong ends or the prong ends do not reach to the crown of that staple, the opposite loops in the adjacent row of staples will seal the blood vessels missed by such prong end spaces. This positioning of prong loops in one row opposite to gaps and prong ends in adjacent rows effects an effective sealing of blood vessels in the mesentery and omentum.

If the first staple of the second row of staples is moved three-quarters of the length of the first staple in the first row, a similar effect will be accomplished except that the prong ends in the first staple of the first row and in the last staple of the second row of staples will not have prong loops in opposite positions. Except for these end defects the three-quarters positioning is considered the equivalent of one-quarter positioning and is covered by claims to the one-quarter positioning.

The staple dimensions given herein apply to the length of the "crown" or the main part of the staple and the prong lengths before being applied or stapled. Typically, for example, vascular staples are presently available commercially with the designation "3.0 mm×2.5 mm (0.118"×0.09")" before closure. The 2.5 mm designation applies to the length of the individual prongs and the 3.0 mm applies to the length of the crown or main body part of the staple. Similarly a larger staple is available with the designation "4.0 mm×4.5 mm (0.157"×0.177")" before closure. Here the prong length is 4.5 mm and the length of the crown before closure is 4.0 mm.

Advantageously the larger prongs are 30–100 percent larger, preferably about 33–50 percent larger than the smaller prongs. The prong lengths will also vary somewhat in accordance with the crown size.

The staple dimensions apply to the length of the main part of the staple before being applied or stapled. For example, vascular staples are available commercially with the designation "3.0 mm×2.5 mm (0.118"×0.098")" before closure. The 2.5 mm designation applies to the length of the individual prongs and the 3.0 mm applies to the length of the main body part of the staple. Similarly a larger staple is available with the designation "4.0 mm ×4.5 mm (0.157"×0.177")" before closure. Here the prong length is 4.5 mm and the length of the main body portion before closure is 4.0 mm.

With the above-mentioned vascular staples, the prong length of 2.5 mm is more than enough to reach the midpoint of the crown which is 1.5 mm from the end of the staple. Therefore the difference or 1 mm is used in forming the loop when the staple is closed. If a semi-circle is drawn at the quarter point in the length of a crown with a radius equal to one-quarter or one-fourth of the crown length, the semi-circle will reach from one end of the crown to the midpoint of the crown. The length of this arc or semi-circle will be ½ the circumference of a circle having a diameter of 1.5 mm which calculates to 1.5 or 1.5×3.1417 or 4.713. The semi-circle will have half this length or 2.356 mm. This is less than the prong length of 2.5 mm. The height of the semi-circle or loop is the length of the line extending perpendicularly from the quarter point of the crown to the semi-circle or loop. Therefore in this case if the prong length is increased, the height of the resultant loop will be increased. If the prong length is decreased, the height of the resultant loop will be decreased.

Similarly with the above-mentioned larger staple, the prong length of 4.5 mm is more than enough to reach the midpoint of the crown which is 2 mm from the end of the staple. Again the difference or 2.5 mm is used in forming the loop when the staple is closed. If a semi-circle is drawn at the quarter point in the length of the crown with a radius of one-quarter or one-fourth of the crown length, the semi-circle will reach from one end of the crown to the midpoint of the crown. The length of this arc or semi-circle will be ½ the circumference of a circle having a diameter of 2 mm will be 2π or 2×3.1417 or 6.2834. The semi-circle will have half this length or 3.1417 mm. This again is less than the prong length of 4.5 mm so that the height of the loop as described above will be considerably greater than for the semi-circle drawn for this staple. Here again if the prong length is increased, the height of the resultant loop will be further increased, and if the prong length is decreased, the height of the resultant loop will be decreased.

A variety of other staples for use on human tissue are also presently available. These vary in crown size and prong size and also in the closeness of the prong ends to the crown.

In the two, three or four rows of staples used in the practice of this invention the crown size is the same throughout and the prong sizes are sometimes varied to give the desired sealing results. As previously mentioned, the staples in one row are staggered at the one-quarter or one-fourth point with respect to staples in the adjacent row or rows. This arrangement effectively positions prong loops opposite gaps between staples or prongs ends in adjacent row or rows of staples.

With the arrangement of parallel adjacent rows of staples of the arrangement described herein, it is possible to staple the mesentery or omentum to stop bleeding from blood vessels as large as 1.0 cm. in diameter down to blood vessels as small as 0.1 mm. in diameter. Moreover these arrangements of staples are found to resist tearing of the fatty tissue of the mesentery and of the omentum. In one modification of the stapler of this invention a cartridge may be used which provides two rows of staples as described above. In another modification of the stapler of this invention a cartridge may be used which provides three rows of staples as described. In still another modification of the stapler of this invention a cartridge may be used which provides four rows of staples as described above. In each case the staples are staggered at the quarter point and preferably at least one row of staples is used which has a different prong size from the other row or rows.

In the stapler of this invention a cartridge containing the staples of described size and arrangement is inserted in the cartridge holder which is opposite and parallel to the anvil portion of the device. The anvil portion has a number of grooves of appropriate size and slope to bend the prongs or the initially perpendicular portions of the staples as they are thrust through the tissue and into the grooves of the anvil whereby the prongs of the staples are turned inward and toward the main portion of the staple. With continued pressure on the stapler, the ends of the staple are pressed close to or against the main portion of the staple with the fatty tissue and the blood vessels pressed in between. Preferably the prongs of the staple when turned back toward the main part of the staple are curved with the ends of the prongs touching or coming into close proximity to the main part of the staple. This curved structure resembles stitching and avoids squeezing the tissue between the prongs and the main part of the staple as would be the case if the prongs were pressed flush against the main part of staple. This reduces the possibility of having the staple cut through the tissue.

SPECIFIC DESCRIPTION OF THE INVENTION

The description of the process stapler and staple cartridge is simplified by reference to the drawings.

FIG. 1 is a front view of a mesentery and the bowel connected thereto.

FIG. 2 is a similar view as in FIG. 1 with three rows of staples across the web or narrow portion of the mesentery.

FIG. 3 is a similar view as in FIG. 1 with three rows of staples halfway across the web and another three rows of staples continuing vertically upward from the first three rows and extending to the bowel.

FIG. 4 is a side, elevational view of a staple positioned above a divided groove in the anvil with the anvil portion shown in cross-section taken by a plane coincident with and extending down from the front surface of the staple.

FIG. 5 is a view similar to that of FIG. 4 after the prongs of the staple have been pressed downward into the grooves of the anvil.

FIG. 6 is a top view of a stapled portion of the mesentery in which three rows of staples having the same size crowns are positioned parallel to each other.

FIG. 7 is a front elevational view of a preferred modification of the stapler of this invention with the staple cartridge portion at its maximum distance from the anvil.

FIG. 9 is a top view of the stapler shown in FIG. 8.

FIG. 10 is an elevational cross-sectional view taken at line 10—10 of FIG. 9.

FIG. 11 is a partial side elevational view of the stapler of FIG. 8 with the positioning rod shown in its farthest position extending into an opening in the anvil holder with a partial cross-sectional view.

FIG. 12 is a cross-sectional view taken at line 12—12 showing the grooves in the anvil.

FIG. 13 is a cross-sectional view taken at line 13—13 showing the staples in the staple cartridge.

FIG. 14 is a side elevational view of a modification of the stapler of this invention in which a replaceable cartridge of staples is used.

FIG. 15 is a cross-sectional view of the stapler of FIG. 14 taken at line 15—15.

FIG. 16 is a side elevational view similar to that shown in FIG. 14 with the cartridge and anvil inserted and the cartridge holder advanced closer to the anvil holder, and with a partial cross-section of the cartridge and cartridge holder.

FIG. 17 is a side elevational view of a staples cartridge suitable for use in the stapler of FIGS. 14-16.

FIG. 18 is a top view of the cartridge of FIG. 17.

FIG. 19 is a rear elevational view of the cartridge of FIG. 17.

FIG. 20 is a cross-sectional view taken at line 20—20 of FIG. 18.

FIG. 21 is a cross-sectional view taken at line 21—21 of FIG. 18.

FIG. 22 is a cross-sectional view taken at line 22—22 of FIG. 18.

FIG. 23 is a view of two rows of enlarged staples 6 of the same crown length and the same prong lengths in which the rows have been moved apart and the staples turned 90° on the crowns as an axis with the staples in the second row each staggered at the midpoint of an adjacent staple in the first row.

FIG. 24 is a view similar to that in FIG. 23 except that the staples of the second row are staggered at the quarter point of the staples in the first row.

FIG. 25 is a view similar to that in FIG. 24 except that a third row is added with staples 7 having shorter prongs than used in the first two rows, the staples in this third row being positioned similarly to those in the first row so that the staples in the second row are also staggered at the quarter point of the staples in the third row.

FIG. 26 is a view similar to that in FIG. 24 except that the staples 7 in the second row have shorter prongs than the staples 6 in the first row.

FIG. 27 is a view similar to that of FIG. 25 except that a fourth row of staples is added with the staples in the fourth row staggered at the quarter point with the staples in the third row.

FIG. 28 is a view of a staple before bending with dotted lines showing in phantom the prong loops formed upon stapling.

FIGS. 29 and 30 are the top and side cross-sectional views respectively of the front end section of a stapler as shown in FIGS. 9 and 10 but adapted to deliver two rows of staples with alternating staples differing in prong length.

FIG. 31 is a forward elevational view of the end portion of the stapler shown in FIGS. 29 and 30 taken at line 31—31 of FIG. 30.

FIG. 32 is a cross-sectional view of the end portion of the stapler shown in FIGS. 29 and 30 taken at line 32—32 of FIG. 30.

FIG. 33 is a view similar to that shown in FIG. 31 except that the grooves in the anvil are adapted to receive staples arranged as in FIG. 26.

FIG. 34 is a view similar to that shown in FIG. 32 showing the end portions of staples arranged as in FIG. 26.

FIG. 35 is a side elevational view of a staples cartridge suitable for use in the end portion of the stapler of FIGS. 29 and 30.

FIG. 36 is a top view of the cartridge of FIG. 35.

FIG. 37 is a rear elevational view of the cartridge of FIG. 35.

FIG. 38 is a cross-sectional view taken at line 38—38 of FIG. 36.

FIG. 39 is a cross-sectional view taken at line 39—39 of FIG. 36.

Figure 8:
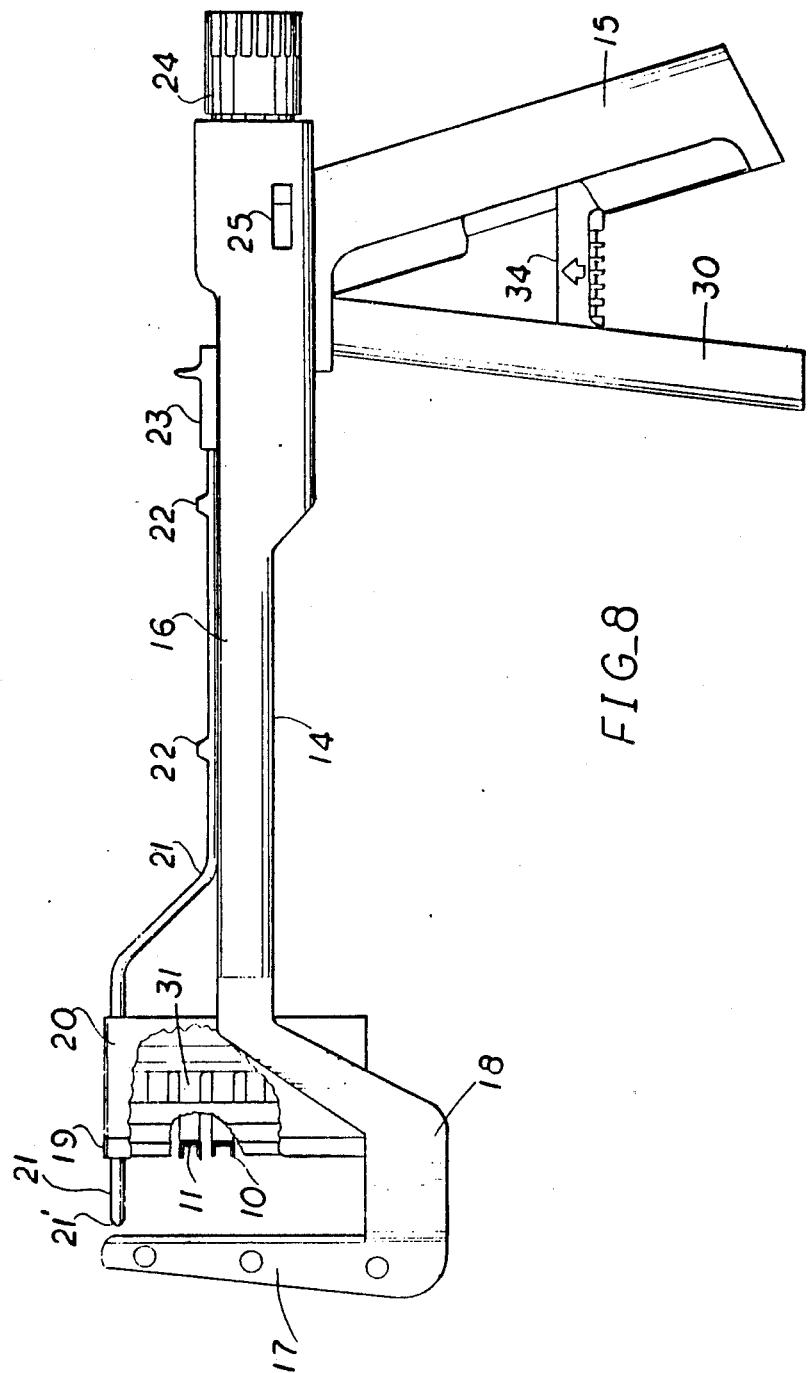
FIG. 8 is a front elevational view similar to that of FIG. 7 with the positioning rod shown advanced to a position closer to the anvil holding portion and the trigger in an open position.

More specifically FIG. 1 shows a mesentery 1 which has the bowel 2 surrounding the greater portion thereof. The base or web 3 of the mesentery has large blood vessels 4 and smaller blood vessels 5 passing therethrough and into the larger part of the mesentery.

FIG. 2 shows the mesentery as shown in FIG. 1 in which three rows of staples of identical crown length have been applied across the web 3 of the mesentery. There are two first rows of staples 6 having prongs longer than the prongs in the third row of staples 7 with the staples in the second row being staggered at the quarter point or ¼th length of the staples in the first and third rows, preferably with very small space between adjacent staples so that the staples in one row overlap the staples in the other row. This arrangement insures that both the small and large blood vessels are compresssed or sealed by this arrangement of staples. Complete blockage of the blood vessels across the width of the web is desirable when the complete bowel is to be removed.

FIG. 3 shows the mesentery in which half of the web has the blood vessels sealed by a similar horizontal arrangement of three rows of staples (two rows with larger prongs and a third row with smaller prongs) with quarterly staggering, and a similar vertical arrangement leading from the midpoint of the web upward to the bowel thereby sealing the blood vessels in that area and thereby accommodating the removal of the left half of the bowel. Lesser or larger portions of the bowel can be accommodated by appropriate changes in the positioning of the three rows of staples as described above.

While it is preferred to have the two rows of larger prongs positioned first with a third row of staples with shorter prongs, it is also contemplated that the two rows of larger prongs may be positioned outside the rows with smaller prongs. Moreover it is also contemplated that there may be a first row of staples with larger prongs and then two rows of staples with smaller prongs. In each case the quarter staggering arrangement is used. In many cases it is also suitable to use a first row with longer prongs and only a second row with shorter prongs, so that there are only two rows of staples. It is preferred however to have at least three rows of staples as described. It is also possible to have the first row, even the first and second rows, comprise staples with shorter prongs with the remaining staples having longer prongs. Also contemplated is the arrangement having two or more rows of staples alternating in each row between longer and shorter prongs.

When reference is made to "first" row of staples this is intended to mean the first row toward that part of the bowel which is to be retained in the patient. The "third"

row, or the "second" row where only two rows are to be used, is that row closest to where the incision is to be made. In other words, this first row is the row farthest from the incision site, and the other outside row is the row closest to the incision site.

FIG. 4 shows a preferred shape of the divided groove 8 in anvil 9 with the staple prongs 10 extending from the crown or main portion 11 of the staple and extending toward anvil groove 8. The depth and shape of the anvil grooves correspond to the length of the prongs to be pressed into the grooves. Shallow grooves are used for shorter prongs and deeper grooves are used for longer prongs.

FIG. 5 shows a preferred curved shape of the prongs 10 after the staple has been pressed against the anvil 9 and into the divided groove 8. As previously stated, this curved shape of the prongs resembles stitching and reduces the pressure that might cut the tissue if uncurved or straight prongs are pressed against the main part 11 of the staple and pressure applied therebetween.

FIG. 6 shows a modification in which three rows of staples are applied, two rows having staples 6 with longer prongs and a third row of staples 7 with shorter prongs.

FIG. 7 gives a front elevational view of a modification of the stapler 14 of this invention which in part resembles a gun with handle 15, barrel 16 and trigger 30. Safety guard 29 is shown in retracted position. Anvil 17 is supported by arm 18 extending from the forward or front end of barrel 16. Staple cartridge 19 is supported by cartridge holder 20. Prongs 10 of the staples are inside the cartridge 19 and are not visible in this view. Positioning rod 21 passes through an opening extending through cartridge holder 20 and also through guides 22 and 22. Knob 23 is fastened to the back end of rod 21 and may advance the forward end of rod 21 to the anvil by pushing knob 23 forward and may retract the rod 21 away from the anvil by pushing knob 23 backward. Cartridge 19 is connected by an arm (not shown here) extending inside barrel 16 and is connected indirectly to knob 24. Knob 24 is capable by a screw arrangement shown in FIG. 10 to advance and retract the cartridge and cartridge holder. Axial rotation in a clockwise direction advances the cartridge holder and cartridge toward the anvil and counterclockwise rotation retracts these away from the anvil. Gap setting 25 allows a measurement of the gap between the anvil and the staple cartridge.

FIG. 8 is a view of the stapler similar to that of FIG. 7 except that the positioning rod 21 has been pushed to a position closer to anvil 17 by forward advancement of knob 23. When the anvil and cartridge are positioned against the tissue to be stapled, further advancement of rod 21 will pierce the tissue by pointed end 21' which will eventually enter an opening (not shown here) in anvil 17 and thereby hold the tissue in position for the stapling operation. Trigger 30 is shown in open position. Closing of trigger 30 toward handle 15 to the position shown in FIG. 7 actuates the forward movement of plunger 27 and plunger arm 32 (neither of which is shown in FIG. 8 but both are shown in FIG. 10) to force the staples into the grooves of the anvil. A partial cross-section of the staple cartridge 19 and cartridge holder 20 shows the staple prongs 10 and staple main portion (or crown) 11 and staple pushers 31 which are moved forward by pusher arm 32. Pusher arm 32 is actuated by plunger arm 27 which is pivotally connected by pin 26 (not shown in FIG. 8 but shown in FIG. 10) to trigger 30 which is pivotally connected by fulcrum pin 33. Before trigger 30 is activated, safety bar 29 is pushed back to its retracted position as shown in FIG. 7.

FIG. 9 is a top view of the stapler of FIG. 8 showing a partial cross-sectional view.

FIG. 10 is an elevational cross-sectional view taken at line 10—10 of FIG. 9. In FIGS. 9 and 10, plunger 27 is connected at one end to cartridge holder 20 and at the other end is pivotally connected to handle trigger 30 by means of pin 26. Trigger 30 is pivotally connected to the upper end of handle 15 by means of fulcrum pin 33. Safety bar 42 is shown in position to prevent premature or accidental movement of trigger 30. When knob 24 is rotated, it is held in position by collar 29 of outer shell 43 while the rotation causes advancement or retraction of screw 28 so that rotation of the threads 35 inside knob 24 in the grooves of screw 28 will cause the desired advancement or retraction of screw 28 which is fixed to base 36 which is fixed to both rod 27 and the top of handle 15. Thus the rotation of knob 24 causes handle 15 and likewise plunger 27, cartridge holder 20 and staple cartridge 19 to advance toward or retract from the anvil 17' in anvil holder 17. The lower edge of outer shell 43 is turned inwardly and horizontally and is slidably mounted in groove 44 in the upper part of handle 15 so that handle 15 can be moved relative to outer shell 43. When staple holder 19 has been positioned against the tissue to be stapled, the stapling action is activated by pressing or squeezing trigger 30. Rods 41 are fixed to outer shell 43 and extend all the way to arm 18 to which anvil 17 is attached.

FIG. 11 is a view of the front part of the stapler of FIGS. 8 and 9 showing the cartridge and cartridge holder 20 in a position closer to the anvil 17' in anvil holder 17.

FIG. 12 is an elevational view of the anvil 17' taken at line 12—12 of FIG. 11. Grooves 8 and 8' are positioned to receive and turn the prongs of the respective staple prongs. The grooves in grooves 8 are deep enough to receive and turn the longer prongs of staples 6 whereas grooves 8' are not as deep as grooves 8 to receive and turn the shorter prongs of staples 7. Opening 37 is an opening in the anvil to receive the end of positioning pin 21. Guide bar 38 is fixed to the anvil holder 17 and is adapted to fit into an opening (not shown) in the cartridge holder.

FIG. 13 is an elevational view of the staple cartridge taken at line 13—13 of FIG. 11. Staples having the longer prongs 6 are in the second and third rows and the staples 7 with shorter prongs are in the first. When inverted the staples 6 will be received and bent in deeper grooves 8 and the shorter prongs of staples 7 are received and bent in more shallow grooves 8'. The staggering of the second row of staples is as described at the quarter point of the staples in the first and third rows. The dimensions of the respective parts of FIGS. 12 and 13 are not according to scale but are exaggerated to show relative positioning. Opening 37' is an opening in the cartridge to allow passage of positioning pin 21. Guide bar 38 fits into an opening in the cartridge holder and insures that the cartridge is correctly positioned with respect to the anvil.

In some cases, such as shown in FIGS. 7-11, the stapler has a staple cartridge as an integral part of the stapler, in which case the whole stapler is discarded once the staples have been applied to the patient. In other cases, such as in FIGS. 14-16, the stapler is adapted to receive replaceable staple cartridges in which case the stapler may be used repeatedly with new cartridges, with sterilization of the gun possible after each use if considered advisable. With the use of the replaceable cartridge the anvil may be an integral part of the stapler or may be a replaceable anvil provided that the grooves in the anvil are registered so that each groove is positioned opposite to the prong which it is to bend. The replaceable anvil is fastened to the anvil holder by means of lips extending from the anvil which slip into slots or grooves in the anvil holder and hold the anvil in the desired registered position.

FIG. 14 is an elevational side view of a stapler 14' in which replaceable staple cartridges and anvils may be inserted. Anvil support arm 18' extends from the front end of barrel 16'. Cartridge holder 20' is attached to a shaft or plunger (not shown) positioned inside barrel 16' positioning pin 21' passes through an opening in cartridge holder 20' and may have its position adjusted by pushing or pulling knob 23'. The position of cartridge holder is adjusted by turning knob 24' which by an internal screw arrangement (not shown) advances or retracts the cartridge holder. Knob 24' is held in position by collar 40' while the screw device in the interior is turned to advance or retract the plunger arm. Trigger 30' is pivotally attached to a plunger arm (not shown) inside the barrel or sleeve 16' and by virtue of fulcrum pin 33' which gives leverage against handle 15' for the purpose of moving the plunger arm inside of barrel 16'. When knob 24' is rotated, it is prevented from moving axially by collar 40' but screw 28' is caused to move out of or into the interior of knob 24' by virtue of reciprocal threads (not shown) in the interior of knob 24'.

FIG. 15 is a cross-sectional view taken at line 15—15 of FIG. 14 showing the screw 28' advanced or retracted by the turning of knob 24' and thereby advancing or retracting plunger 27'.

FIG. 16 is another side elevational view of the stapler of FIG. 14 with a partial cross-sectional view of the cartridge holder 20' and of the cartridge 19' shown inside the cartridge holder with a row of staples 6'.

FIG. 17 is a side elevational view of a replaceable cartridge showing the first row of staples 6' in partial cross-sectional view, suitable for use in the stapler of FIGS. 14–16 showing plunger manifold arm 34'" and individual plungers 34"". Staple holder 39' has the three rows of staples held in the interior thereof.

FIG. 18 is a top view of the staple cartridge of FIG. 17 showing manifold plunger 34'" and three rows 34"", 34"" and 34"" of individual plungers for the shorter pronged staples, longer pronged staples, and longer pronged staples respectively.

FIG. 19 is a rear view of the cartridge of FIG. 17.

FIG. 20 is a cross-sectional view taken at line 20—20 of FIG. 18 showing a row of the staples 7' having shorter prongs.

FIG. 21 is a cross-sectional view taken at line 21—21 of FIG. 18 showing the row of staples 6' having longer prongs.

FIG. 22 is a cross-sectional view taken at line 22—22 of FIG. 18 showing a row of staples 6' having longer prongs.

FIG. 23 shows two rows of staples with longer prongs which have been separated a sufficient distance to allow each row to be turned 90° on the axis of the staple crowns so that the relative positions of the prong loops and open gaps may be represented. In FIG. 23 the staples in the second row are staggered at the midpoint of the adjacent staples in the first row. This view shows that the loops in the second row are not appropriately positioned to embrace blood vessels that have come through the gaps in the first row of staples.

FIG. 24 shows a similar two rows of staples except that the staggering in the second row starts opposite the quarter point in the staples of the first row.

FIG. 25 shows a preferred arrangement in which two rows of staples with longer prongs arranged as in FIG. 24 have been supplemented with a third row of staples 7 with shorter prongs. This shows how the quarterly staggering in each row provides loops in the second row to seal blood vessels which may have come through gaps in the first row.

FIG. 26 shows two rows of staples in which the staples in the first row have longer prongs than the prongs in the second row.

FIG. 27 shows an arrangement of a first two rows of staples 6 having longer prongs followed by two rows of staples 7 having shorter prongs, in each row the staples have the quarterly staggering arrangement with staples in the adjacent row or rows.

FIG. 28 shows a staple with crown 40 and prongs 41. Phantom lines 42 show the loops that will be formed upon stapling. Line 43 represents the rise or the distance on a line perpendicular to the crown at the quarter point of the crown. As discussed above, this rise will increase in length with increase in prong length and will decrease in length with decrease in prong length. With long prongs it is advantageous to have a rise greater than 1 mm and with shorter prongs it is advantageous to have a rise lower than 0.75 mm.

In the preceding figures the effectiveness of the staples for sealing off the various sized blood vessels in the mesentery are dependent on using rows of staples in which the crowns of these staples in a particular row are of identical size but there is a staggering arrangement by which prong loops are positioned opposite to gaps in an adjacent row of staples and therefore capable of embracing and sealing blood vessels that may have escaped sealing by a prior row of staples.

FIG. 29 is a top view similar to that shown in FIG. 9 but for a stapler designed to staple two rows of staples in which each row of staples are of alternating prong length.

FIG. 30 is a side elevational cross-sectional view taken at line 30—30 of FIG. 29.

FIG. 31 is a forward elevational view taken at line 31—31 of FIG. 30.

In the arrangement shown in FIGS. 29 and 30 the operation of the complete stapler is the same as for the stapler shown in and described for FIGS. 9 and 10. Plunger arm 27 advances cartridge holder 20 and causes staple cartridge 19 to advance toward or retract from anvil 17' in anvil holder 17. In identical manner the stapling action is activated by squeezing trigger 30 (shown in FIG. 10).

FIG. 32 is a rearward elevational view taken at line 32—32 of FIG. 30.

FIG. 33 is a similar view to that shown in FIG. 31 except that the anvil grooves are adapted for use with staples arranged as in FIG. 26 (now arranged vertically instead of horizontally as shown in FIG. 26).

FIG. 34 is a similar view to that shown in FIG. 32 except that the staples are arranged as in FIG. 26 (now arranged vertically instead of horizontally as in FIG. 26).

FIG. 35 is a side elevational view of a replaceable cartridge showing the first row of alternating staples 6 with shorter prongs and staples 7 with longer prongs in partial cross-sectional view, suitable for use in the stapler of FIGS. 14–16 modified as in FIGS. 29 and 30 showing plunger manifold arm 44. Staple holder 47 has the two rows of staples held in the interior of cartridge 48.

FIG. 36 is a top view of the staple cartridge 48 of FIG. 35 showing manifold plunger 44 and individual plungers 45 for the staples 6. Staple holder 39' has two rows of staples.

FIG. 37 is a rear view of the cartridge of FIG. 35.

FIG. 38 is a cross-sectional view taken at line 38—38 of FIG. 36 showing a row of the staples 6 with longer prongs.

FIG. 39 is a cross-sectional view taken at line 39—39 of FIG. 36 showing the row of staples 7 with shorter prongs.

The views of staples, cartridges, etc., are not according to scale but are merely illustrative and may be out of proportion since it is difficult to depict exact proportions. Moreover the number of staples in a cartridge is also not representative and may vary considerably from those shown in the figures.

The prongs generally have lengths in the range of ½ to 1 1/5 the length of the main portions or crowns of the respective staples. Thus the smaller prongs advantageously have lengths of about 1.0 to 2.75 millimeters and the larger prongs have lengths of about 1.5 to 6.0 millimeters in length.

When there are only two rows of staples the distance between rows is advantageously between 1.5 and 3 millimeters. The distance between the first and third rows of staples is advantageously a maximum of about 6 millimeters and a minimum of about 3 millimeters, preferably this distance is about 4 millimeters, and the second row of staples is advantageously about midway between the first and third rows. When there is a fourth row of staples, the distance between the third and fourth rows is generally approximately the same as between the other adjacent rows.

The staples themselves may be made of any appropriate material that is capable of being bent in the manner described and has the strength to hold its shape once bent, provided the material does not produce an adverse effect on or cause infection of the tissue on which it is being used. Preferably the staples are of stainless steel of the same type as is presently being used in the vascular staples.

In applying the staples the stapler is positioned adjacent to the appropriate part of the mesentery or omentum with the jaws of the anvil and the staple cartridge on opposite sides of the tissue to be stapled. Then the pointed positioning rod 21 is pushed by means of knob 23 so that the tissue is pierced by this pointed rod and the end of rod 21 rests in opening 25 of the anvil so that the tissue is fixed in position with respect to the stapler. Then the cartridge 19 and cartridge holder 20 are advanced by axial rotation of knob 24 to a position where the cartridge is pressed against the tissue. Then the staples are applied to the tissue and bent into set shape by pressure actuated by the pressing of trigger 30. After the staples have been applied, the rod 21 is retracted by pressing backward on knob 23 and the stapler is removed.

The stapler and cartridges shown in the drawings are specified to two or three rows of staples. Obvious modifications can be made to staples and cartridges to provide the various arrangements of staples shown in FIGS. 23–27 and the anvils in the stapler will be modified to receive and bend the prongs of the respective sizes and positions of the staples being applied.

In the drawings the staples are generally represented with heavy lines instead of the outline form and sometimes in order to avoid confusion background material has been omitted.

In the stapler of this invention it is important that the edges, particularly on the front of the stapler, should be well rounded to avoid tearing the tissue with which it may come into contact.

In summary, for use in the stapler, in the cartridge and in the process of this invention, the staples used should have the same dimension in the crown or main portion, that is the portion connecting the two prongs, advantageously in the range of 2.5 to 4.5 millimeters, preferably 3–4 millimeters, having this dimension in the range of 2.5 to 3.5 millimeters and the larger staples having this dimension in the range of 3.5 to 4.5 millimeters, the larger prongs preferably being at least 30 percent longer in this dimension than the smaller prongs. The gaps or distances between adjacent staples in a particular row are the same as used in present day practice, generally in the range of 1–2.5 mm, preferably 1–2 mm.

While the above descriptions have related to rows of staples having the same crown length, it is also contemplated that these may be supplemented by the addition of one or two rows of staples in which the crown size differs from those in the first two or three rows of staples having the same crown length and arranged with the quarter length staggering described above. With different crown lengths the staggering cannot be effected throughout except with another row of staples with the same crown length. As an example of a supplemental row or rows of staples having different crown length, the arrangement of FIG. 24 or FIG. 26 may be supplemented by the addition of one or two rows of staples having a shorter or longer crown length. It is contemplated that claims directed to the arrangement of FIG. 24 or FIG. 26 would cover the two rows of such Figures with or without the one or two supplemental rows.

The following examples illustrate the ineffectiveness of two and three rows of staples of the same size crown and prongs and arranged with staggering at the midpoint of staples in adjacent rows. Also are examples of how the shifting of the staggering to the quarter point of the staples in the adjacent row will improve the effectiveness in sealing off blood vessels in the mesentery.

EXAMPLE I

In an operation on the mesentery of a patient, the surgeon affixes two parallel rows of staples having 3.0 mm crown and 2.5 mm prongs with the staples in the second row staggered with the beginning end of each crown in the second row positioned opposite the midpoint of the crown in the adjacent staple in the first row, as illustrated in FIG. 23. Upon cutting the mesentery distal to the stapled lines, there is profuse bleeding requiring clamping and ligation in the traditional manner to effectively stop the blood flow. This procedure is repeated in three subsequent operations on the mesentery with similar results in each case.

EXAMPLE II

In another operation on a patient for whom a part of the bowel and adjoining part of the bowel are to be removed, the surgeon carefully affixes two parallel rows of staples having 4.0 mm crown and 4.5 mm prongs with the beginning end of each crown in the second row positioned opposite the midpoint of the crown in adjacent staple in the second row, as illustrated in FIG. 23. When an incision is made across the area of the mesentery to be resected distal to the staple lines and after removal of the bowel and mesentery sections, the incision is inspected for leakage. It is found that there is profuse blood leakage and it is necessary to clamp the blood vessels individually and to ligate them in the traditional manner to stop the flow of blood.

EXAMPLE III

In an operation upon a patient for whom a part of a bowel and adjoining mesentery are to be removed, the surgeon carefully affixes across the mesentery three parallel rows of the staples described above in Example II. Each staple in the middle row is staggered with the beginning point of each staple in the middle row positioned opposite the midpoint of the adjacent staples in the first and third rows. An incision is made across the area of the mesentery to be resected distal to the staple lines. After the sections of the mesentery are removed, the stapled area is carefully inspected to determine if the incision is properly sealed. It is found that there is profuse blood leakage and that the incision is not sealed within the recognized standard of medical care. It is then necessary to clamp the bleeding blood vessels individually and to ligate them in a traditional manner to stop the flow of blood.

EXAMPLE IV

In an operation upon a patient for whom a part of the bowel and adjoining mesentery are to be removed, the surgeon carefully affixes across the mesentery two parallel rows of staples having crown size of 4.0 mm and prong size of 4.5 mm with the staples in the second row staggered so that the beginning point of each crown is positioned opposite the quarter point of the adjacent staple in the first row, in accordance with the arrangement shown in FIG. 24. There is a marked improvement in the sealing effectiveness of the stapling with no blood leakage.

EXAMPLE V

In an operation upon a patient for whom part of the bowel and adjoining mesentery are to be removed, the surgeon carefully affixes across the mesentery three parallel rows of staples. In the first two rows the staples have crowns of 4.0 mm and prongs of 4.5 mm and the third row has crowns of 4.0 mm and prongs of 3.5 mm. Each staple in the second row is staggered at the quarter point of adjacent staples in the first and third rows as shown in FIG. 25. Then after an incision is made distal to the three lines of staples and removal of the sections of mesentery and bowel, inspection is made of the stapled incision and it is found that the incision is properly sealed within the recognized standard of medical care.

EXAMPLE VI

The procedure of Example IV is repeated using staples having a crown size of 4.0 mm in both rows with the prong size in the first row being 4.5 mm and in the second row being 3.5 mm and the staggering being at the quarter point as illustrated in FIG. 26. Then after an incision is made distal to the two rows of staples and removal of the sections of mesentery and bowel, inspection shows that the incision is properly sealed within the recognized standard of medical care.

While reference is made herein to quarterly staggering or staggering at the quarter point of adjacent staples in an adjacent row, it is intended that there may be some variation from the quarterly staggering. Such variations will be suitable so long as the loops formed by the prongs in one row will be opposite gaps in an adjacent row of staples. This variation is covered by the expression "substantially at the quarter point".

Furthermore, while the description of quarterly staggering refers to the second row of staples being staggered at the quarter points of adjacent staples in the first row, it is equally effective and equivalent to have the first row arranged at the quarterly points of staples in the second row. This may be demonstrated by reference to FIG. 24. Thus by interchanging the two rows of staples, the staples of the new first row (formerly second row) would have the beginning of the crowns positioned at the quarter points of the respective adjacent staples in the new second row (formerly first row). The important feature is that a loop in one row of staples is opposite a gap in the adjacent row of staples.

In summary, staples suitable for use in the practice of this invention advantageously have crown lengths in the range of 2.5 to 4.5 mm, preferably 3-4 mm. Prong lengths are selected in accordance with the crown length and the rise desired in the prong loops, and are advantageously in the range of 1 to 6 mm, preferably in the range of 2 to 5 mm.

While certain features of this invention have been described in detail with respect to various embodiments thereof, it will of course be apparent that other modifications can be made within the spirit and scope of this invention, and it is not intended to limit the invention to the exact details insofar as they are defined in the following claims.

What is claimed is:

1. In a stapling device designed for use on a patient which comprises:
   (a) a handle by which the device may be held in the operator's hand;
   (b) a sleeve having a forward and a rear end thereto, which sleeve is connected at a point near its rear end to said handle at an angle of about 90°-100°, at which point said handle is slidably mounted at the interior of said sleeve, and said sleeve having a knob extending from the rear end thereof;
   (c) a shaft extending lengthwise and inside said sleeve and being connected at one end to said handle adjacent to the area where said handle is slidably mounted on said sleeve;
   (d) an adjusting means for advancing said shaft toward the forward end of said sleeve and for retracting said shaft toward the rear end of said sleeve, said adjustment being effected by the axial rotation of said knob extending from the rear end of said sleeve;
   (e) a cartridge holding means attached to and positioned perpendicularly from the opposite end of said shaft from the end connected to said handle, said cartridge holding means being capable of being advanced and retracted with said shaft movement;

(f) a support means extending downward and forward from the front end of said sleeve;

(g) an anvil held by said support means in a position parallel to and opposite to said cartridge holding means;

the improvement whereby said stapler device is suitable for use on a patient's mesentery which comprises:

(h) a cartridge positioned on said cartridge holding means having at least two and no more than four parallel rows of staples, each staple having crown and two prongs each prong being attached to an end of said crown, each intermediate row of staples being substantially equidistant from adjacent rows, with the staples in each row having the same length of crown and each crown being staggered at the quarter point in the length of the crown of the adjacent staple in the adjacent row of staples; whereby the ends of looped prongs are opposite the approximate mid-point of a looped prong on an adjacent row, and (i) an anvil having grooves therein spaced from and positioned opposite to and facing the prongs of the staples in said cartridge and positioned to receive and to turn the prongs of each said staple toward each other and toward the crown of said staple.

2. The device of claim 1 in which the staples in at least one of said rows of staples has prongs of a different size from the other staple prongs in said rows of staples.

3. The device of claim 2 in which the depth of said grooves vary in depth in accordance with the length of the prongs to be bent in said grooves whereby the said prongs will be bent into loops having the prong ends near the midpoint of the crown to which the prongs are attached.

4. The device of claim 3 in which said cartridge has three rows of staples, the staple prongs in the first two rows having the same size and the staple prongs in the third row having a different size from the staple prongs in the said first two rows.

5. The device of claim 3 in which said cartridge has four rows of staples, the staple prongs in the first two rows having the same size and the staple prongs in the third and fourth rows having a different size from the staple prong in the said first two rows.

6. The device of claim 4 in which the staple prongs in said first two rows have a larger size than the staple prongs in said third row.

7. The device of claim 5 in which the staple prongs in said first two rows have a larger size than the staple prongs in said third and fourth rows.

8. The device of claim 3 in which said cartridge has three rows of staples, the staple prongs in the second row having a size different from the prongs in the first of said row of staples.

9. The device of claim 8 in which the staple prongs in second row are smaller than the prongs in the first of said rows.

10. The device of claim 8 in which the staple prongs in the second and third rows are smaller than the prongs in the first of said rows.

11. The device of claim 3 in which said cartridge has two rows of staples, the prong lengths in the staples of both rows are of the same size.

12. The device of claim 3 in which said cartridge has two rows of staples, the prong lengths in the second row of staples differing in size from the prongs of the first row.

13. The device of claim 12 in which the size of the prongs in said second row of staples is smaller than the size of the prongs in the first row of staples.

14. A cartridge of staples suitable for use in a stapling device having at least two and no more than four parallel rows of staples, each staple having the same length of crown and each crown being staggered at the quarter point in the length of the crown of the adjacent staple in the adjacent row of staples.

15. The cartridge of claim 14 in which there are three rows of staples, the prong lengths in at least one of said rows of staples differing in size from the staples in the remaining rows.

16. The cartridge of claim 15 in which the prong lengths in at least one of said rows are shorter than the prong lengths in the remaining rows.

17. The cartridge of claim 14 in which there are two rows of staples.

18. The cartridge of claim 17 in which the prong size in one row differs from the prong size in the other row.

* * * * *

UNITED STATES PATENT AND TRADEMARK OFFICE
CERTIFICATE OF CORRECTION

PATENT NO. : 4,941,623

DATED : July 17, 1990

INVENTOR(S) : J. Crayton Pruitt

It is certified that error appears in the above-identified patent and that said Letters Patent is hereby corrected as shown below:

In the Abstract, line 10, correct "pront" to read "prong".

Col. 5, line 21, change "1.5" (first appearance to read "1.5 $\pi$".

Signed and Sealed this

Eighteenth Day of December, 1990

Attest:

HARRY F. MANBECK, JR.

*Attesting Officer*     *Commissioner of Patents and Trademarks*